(12) United States Patent
Riley et al.

(10) Patent No.: US 6,573,284 B1
(45) Date of Patent: Jun. 3, 2003

(54) METHOD OF TREATING MELANOMA

(76) Inventors: Patrick Anthony Riley, 2 The Grange, Grange Avenue, London (GB), N20 8AB; Andrew Photiou, 68 St. Augustine's Road, London (GB), NW1 9RP; Tariq Hussain Khan, 36 Southmill Road, Bishop Stortford, Hertfordshire (GB), CM23 3DP; Helen Mary Osborn, 36 Southmill Road, Bishop Stortford, Hertfordshire (GB), CM23 3DP (*) Notice: Subject to any disclaimer, the term of this patent is extended or adjusted under 35 U.S.C. 154(b) by 0 days.

(21) Appl. No.: 09/319,866
(22) PCT Filed: Dec. 12, 1997
(86) PCT No.: PCT/GB97/03433
§ 371 (c)(1), (2), (4) Date: Jun. 21, 2000
(87) PCT Pub. No.: WO98/25886
PCT Pub. Date: Jun. 18, 1998

(30) Foreign Application Priority Data

Dec. 13, 1996 (GB) .............................................. 9625895

(51) Int. Cl.[7] .......................... A61K 31/44; A61K 31/27
(52) U.S. Cl. ........................ 514/346; 514/211; 514/245; 514/356; 514/357; 514/487; 514/492; 514/565; 514/585; 514/587; 514/595; 514/599
(58) Field of Search .................................. 514/211, 245, 514/346, 356, 357, 487, 492, 565, 585, 587, 595, 599

(56) References Cited

U.S. PATENT DOCUMENTS

| | | | |
|---|---|---|---|
| 3,592,836 A | | 7/1971 | Ugi et al. .................... 260/463 |
| 3,796,723 A | | 3/1974 | Kaiser et al. ........... 260/326.11 |
| 4,115,539 A | | 9/1978 | Eisenhardt, Jr. et al. ......... 424/1 |
| 4,812,590 A | * | 3/1989 | Saari et al. .................. 560/137 |
| 5,767,237 A | * | 6/1998 | Sakakibara et al. ......... 530/330 |

FOREIGN PATENT DOCUMENTS

| | | |
|---|---|---|
| DE | 2 424 540 | 12/1974 |
| DE | 24 48 257 A | 4/1976 |
| EP | 0584 552 A | 3/1994 |
| EP | 0 604 278 A | 6/1994 |
| EP | 696593 | * 2/1996 |
| GB | 1 365 702 | 9/1974 |
| WO | WO 95/09841 | 4/1995 |

OTHER PUBLICATIONS

Rodriguez et al., "The Structures And Sterochemistry Of Cytotoxic Seqquiterpene Quinones From *Dactylospongia Elegans*," *Tetrahedron*, vol. 48, No. 32, pp. 6667–6680, 1992.

Chemical Abstracts, vol. 084, No. 3, Jan. 19, 1976, abstract No. 012419, Sidorik et al., "Antineoplastic properties of 2-phenazinylthioureidotyrosine".

Hong et al., "Synthesis And Biologica Activity Of Analogs Of Naturally Occurring 6–Ureidopurines And Their Nucleosides," *Journal of Medicinal Chemistry*, vol. 16, No. 2, pp. 139–147, 1973.

Burke et al., "Hydroxylated Aromatic Inhibitors of HIV–1 Integrase," *J. Med. Chem.*, vol. 38, No. 21, pp. 4171–4178, 1995.

Panigrahi et al., "Toward a Mechanism–Based Fluorescent Assay for Site–Specific Recombinases and Topoisomerases: Assay Design and Synthesis of Fluorescent Substrates," *J. Am. Chem. Soc*, vol. 118, No. 48, pp. 12004–12011, 1996.

Robbins et al., "Forskolin Carbamates: Binding and Activation Studies with Type I Adenylyl Cyclase," *J. Med. Chem.*, vol. 39, pp. 2745–2752, 1996.

Chemical Abstracts, vol. 118, No. 20, May 17, 1993, Abstract No. 204428 Pyra et al., "Chromatographic separation of some monoamines in the form of 4–N, N–dibutylaminoazobenzene–4'–thiocarbam oyl".

Chemical Abstracts, vol. 97, No. 8, Aug. 23, 1982, No. 65714 Mancheva et al., "Possible amino acid analysis of peptide hydrolysates".

Database WPI, Section Ch, Week 9521, Derwent Publications Ltd., Mar. 28, 1995.

Cooksey et al., "Tyrosinase–Mediated Cytotoxicity of 4–Substituted Phenols: Use of QSAR to Forecase Reactivities of Thiols towards the Derived ortho–Quinones," *Quantitative Structure–Activity Relationships*, vol. 15, pp. 498–503, 1996.

* cited by examiner

*Primary Examiner*—Bernard Dentz

(57) ABSTRACT

Novel pro-drugs and assay reagents are provided which are useful as therapeutic agents especially for delivery and targetting therapeutically active agents to melanoma cells. The pro-drugs and assay reagents are substrates for tyrosinase and may be represented by the formula TyrX—B—ThrAg*. The compounds of formula TyrX—B—ThrAg* are capable of releasing a therapeutically active agent or assayable substance (ThrAg) at a desired location. TyrX— being a residue of an optionally substituted tyrosine analogue.

Scheme 1: Synthesis of Prodrug A

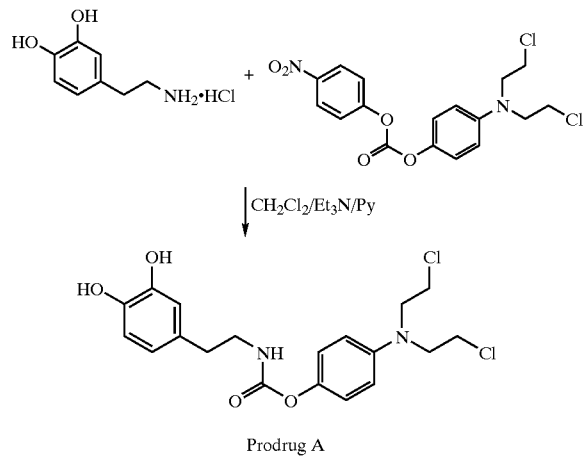

Prodrug A

8 Claims, 9 Drawing Sheets

MASS SPECTRA

METHOD OF TREATING MELANOMA

This application is a 371 of PCT/GB97/03433 filed Dec. 12, 1997.

The present invention relates to novel compounds useful as therapeutic agents and assay reagents. More specifically, the present invention relates to a drug targeting and especially to a novel method of delivery of therapeutically active agents to tumour cells, in particular melanoma cells.

BACKGROUND TO THE INVENTION

Malignant melanoma is an important cancer with a rising incidence world-wide affecting people of all ages, including a relatively young population. Whilst progress is being made in prevention and in early diagnosis, the major problem is the difficulty of treating the disease in its disseminated state. Therapeutic agents with improved effectiveness are urgently required if the number of deaths resulting from malignant melanoma is to be reduced. Melanoma has the potential of rapid metastasis and remains a difficult neoplasm to treat. Conventional antineoplastic agents continue to be of value in the management of this malignancy but improved clinical results can be achieved if established or newly discovered agents are modified to allow them to act more selectively. The delivery of cytotoxic agents to the site of tumour cells is much desired because systemic administration of these agents often results in the killing of normal cells within the body as well as the tumour cells sought to be eliminated.

Sadly, treatment of disseminated melanoma is currently inadequate, remaining incurable. Targeted chemotherapy seems a feasible approach for this neoplasm because in the adult human melanogenesis is uniquely a property of melanocytes. Previous attempts at utilization of the melanogenic pathway to activate prodrugs have made use of the formation of reactive quinone intermediates which rely on thiol depletion for their toxic effect and initial attempts to treat melanoma in the clinic have been unsuccessful due to unfavourable pharmacokinetics, low potency and systemic toxicity.

In developing the compounds of the invention, reliance was placed on the realisation that the tyrosinase enzyme is differentially associated with certain target cells, especially melanoma cells.

Thus, tyrosinase (monophenol, 3,4-dihydroxyphenylalanine: oxygen oxidoreductase, EC 1.14.18. 1) is generally exclusive to pigment-producing cells (melanocytes) and is frequently unregulated in melanoma. Use of the catalytic potential of tyrosinase to generate a highly toxic compound from a non-toxic substrate or "prodrug" has been suggested [see Riley P A (1991) Eur J Cancer, 27: 1172–1177] and so far, a number of potential melanoma prodrugs have been studied, but with limited success. Examples of such agents include analogues of tyrosine which are oxidised by tyrosinase to generate cytotoxic quinones [see e.g. Naish S, Cooksey C J & Riley P A (1988) Pig. Cell Res., 1:3 79–381; Naish S, Holden J L, Cooksey C J & Riley P A (1988) Pig. Cell Res, 1:382–385] which act through mechanisms leading to thiol depletion [see e.g. Alena F, Iwashina T, Gili A & Jimbow K (1994) Cancer Res., 54(10): 2661–2666; Alena F, Dixon W, Thomas P & Jimbow K (1995) J. Invest. Dermatol., 104(5): 792–797; Riley P A, Cooksey C J, Johnson C I, Land E J, Latter A M & Ramsden C A (1996) Eur. J. Canc. (in press)].

Initial studies indicated that compounds such as 4-hydroxyanisole held promise in targeted melanoma chemotherapy [see Morgan B D G, O'Neill T, Dewey D L, Galpine A R & Riley P A (1981) Clin. Oncol., 7:227–234], but a number of serious difficulties have been encountered in the clinic, notably the relatively limited cytotoxicity of the resulting cytotoxic quinone, necessitating the use of high serum levels of the prodrug and complications from systemic actions [see Rustin G J, Stratford M R, Lamont A, Bleehen N, Philip P A, Howells N, Wafta R R & Slack J A (1992) Eur. J. Canc., 28A, 1362–1364; Belcher H J, Nizam M & ONeill T J (1992) Br. J. Plast. Surg., 45:208–210] due to alternative metabolism, particularly hepatic and renal toxicity [see Schiller C D, Gesher A & Jheeta P (1991) Eur. J. Canc., 27:1017–1022; Stolze K & Nohl H (1991) Free Rad. Res. Comm., II:321–327. Refs. 17,18].

Therefore, in order for tyrosinase-dependent activation of cytotoxic pro-drugs is to become an effective and realistic chemotherapeutic targeting strategy for the treatment of melanoma, there has been a need for agents to be developed that produce their action by a mechanism that does not rely for its cytotoxic effect on thiol depletion.

The basis of our new approach to lethal synthesis in melanogenic cells, which to our knowledge has not hitherto been studied, is the utilization of the reductive cyclization process associated with the tyrosinase enzyme to initiate the specific intracellular release of cytotoxic agents. By this approach, we have succeeded in incorporating in a prodrug known cytotoxic compounds whose behaviour on release are well understood and which have been proven as potent inhibitors of tumour growth. The modification of the chemical structure of the active agent by incorporation in the prodrug is designed to moderate its cytotoxicity whilst it is in the form of the prodrug by diminishing its reactivity and by reduction of systemic bioavailability through effects on half-life or altered cellular uptake characteristics. The targetted release mechanism proposed is aimed at selectively liberating the drug from these constraints.

It is one aim of the present invention to produce and screen a novel category of anti-melanoma compounds. A further object is to provide novel compounds useful as assay or diagnostic agents. The approach that we adopted was based on our appreciation that the structural requirements for compounds to act as substrates for tyrosinase could be adapted to the synthesis of prodrugs.

SUMMARY OF THE INVENTION

The present invention provides a novel class of compounds which depend upon the action of tyrosinase for their conversion to desired products, including therapeutically active substances and assayable metabolites, e.g. indicator molecules.

Thus according to one aspect of the invention there is provided a pro-drug which is capable of releasing a therapeutically active agent at a desired location, characterised in that the pro-drug is a substrate for tyrosinase wherein in the presence of tyrosinase, the compound is oxidised to a quinone, which undergoes cyclisation and hydrolysis to release therapeutically active agent.

According to a further aspect of the invention there is provided a compound which is capable of conversion to an assayable substance such as an indicator molecule, characterised in that the compound is a substrate for tyrosinase wherein in the presence of tyrosinase, the compound is oxidised to a quinone, which undergoes cyclisation and hydrolysis to release said assayable substance.

More specifically, the invention provides a compound, in particular a prodrug, which is capable of releasing a therapeutically active agent or assayable substance (ThrAg) at a desired location, characterised in that the compound is a substrate for the tyrosinase enzyme and has the formula:

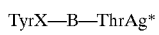

TyrX—B—ThrAg* wherein TyrX— is a residue of an optionally substituted tyrosine analogue of the structure

wherein each of the symbols =Z— is independently selected from =CH—, =C—, =N—, and —$N^+$=O, B represents a linking group or single bond linking TyrX and ThrAg*, ThrAg* represents a residue of a therapeutically active agent ThrAg or a residue of an indicator molecule, and Y represents —O—, —S— or a group

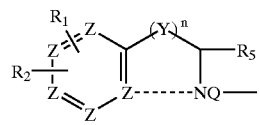

n is 1, 2, 3 or 4 (preferably 1 or 2), and either NQ— represents —N— and the dotted line represents a bond linking the nitrogen atom to the indicated ring atom or NQ— represents —$NR^6$— and the dotted line is to be ignored, $R^1$ and $R^2$ independently represents hydrogen, halogen (e.g. F, Cl, Br or I) or —OH, $R^3$, $R^4$, and $R^5$ independently represent hydrogen, halogen (e.g. F, Cl, Br or I), $C_{1-4}$ alkyl, $C_{1-4}$ alkenyl, $CF_3$, $NO_2$, —OH, —COOH, —COOR, or —$CH_2OH$, wherein R represents $C_{1-4}$ alkyl, and $R^6$ represents hydrogen, halogen (e.g. F, Cl, Br or I), $C_{1-4}$ alkyl, $C_{1-4}$ alkenyl, $CF_3$, $NO_2$, —OH, —COOH, —$CH_2OH$, —COOR, —OR, —SR or —SeR wherein R represents $C_{1-4}$ alkyl, and wherein in the presence of tyrosinase, the compound TyrX—B—ThrAg* is oxidised to a quinone, which undergoes cyclization and hydrolysis to release ThrAg.

$R^1$ and $R^2$ are preferably selected from H and OH. $R^3$ and $R^4$ are preferably selected from H and —$CH_3$, $R^5$ is preferably selected from H or —COOH, $R^6$ is preferably selected from H, $CH_3$ and —$OCH_3$.

Most preferably, TyrX is an optionally substituted tyrosine analogue having one of the following structures, wherein =Z—, NY, Q, B, $R_1$, $R_2$, $R_3$, $R_4$, $R_5$, $R_6$ and n are as defined above -continued Examples of linking groups B include:

and

A novel feature of the prodrugs provided in accordance with the invention is the mechanism by which the therapeutically active agent or assayable substance ThrAg is released, allowing in the case where the compound of the invention is a prodrug, targeted delivery of therapeutically active agent. This is based on attachment of the selected agent to the nitrogen atom of the structure TyrX—. This nitrogen atom is involved in cyclization following oxidation by the tyrosinase enzyme, resulting in formation of a group that is susceptible to hydrolysis. On tyrosinase-catalysed oxidation of the pro-drug to the quinone, cyclization produces a positively charged species which undergoes hydrolysis releasing the drug.

This mechanism is analogous to the initial phase of melanogenesis which involves the tyrosinase-catalysed oxidation of tyrosine whereby tyrosine is oxidised to the corresponding orthoquinone, which is susceptible to nucleophilic attack. A major pathway involves endogenous cyclization by reductive addition to the ring brought about by the presence of the nucleophilic amino function in the side chain to give rise to cyclodopa.

The manner in which the therapeutically active agent or assayable substance ThrAg is chemically linked to the residue of the optionally substituted tyrosine analogue TyrX— will depend upon the structure of ThrAg and in particular on the availability of chemically reactive groups therein.

Thus for example, if the therapeutically active agent or assayable substance ThrAg contains a carboxy group —COOH, ThrAg may be linked to the optionally substituted tyrosine residue TyrX— by formation of an amide linkage, TyrX—NH.CO—ThrAg*. Examples of therapeutically active agents which contain carboxy groups include betulinic acid and retinoic acid.

Alternatively, if the therapeutically active agent or assayable substance ThrAg contains a hydroxy group —OH, ThrAg may be linked to the optionally substituted tyrosine residue TyrX— by formation of an urethane linkage, TyrX—NH.CO.O—ThrAg*.

Examples of therapeutically active agents which contain hydroxy groups include oxaliplatin derivatives, vinca alkaloid S12363, quercitin, genistein, calcipotriol and 4-hydroxy anisole.

By way of further example, if the therapeutically active agent or assayable substance ThrAg contains a primary or secondary amino group —$NH_2$ or —NH—, ThrAg may be linked to the optionally substituted tyrosine residue TyrX— by formation of secondary or tertiary amino linkages TyrX—NH—ThrAg* or TyrX—N=ThrAg*. Examples of therapeutically active agents which contain primary or secondary amino groups include dacarbazine, nifedipine, staurosporin and N-methylarginine.

More generally, the abbreviation "ThrAg" can refer to any therapeutically active agent (e.g. a cytotoxic agent), or assayable substance (e.g. an indicator molecule for use in an assay) that can be chemically modified into the pro-drug TyrX—B—ThrAg*. Further classes of therapeutically active agents and assayable substances ThrAg include:

- chemosensitising agents, i.e. chemicals that can make tumour cells sensitive to cytotoxic agents:
- resistance or multidrug resistance (MDR) modifiers, i.e. chemicals that can reverse the effect of multidrug resistance expression in refractory tumour cell lines, leading to a re-sensitisation of the tumour cells to MDR drugs:
- immunostimulating agents, i.e. chemicals that can prime the immune system, thus triggering an immune system against the tumour, either directly or indirectly incorporation of cytokines into a prodrug structure which can have immunomodulatory activity or other direct/indirect inhibitory actions on cancer cells
- signal transduction inhibitors, i.e. chemicals that can selectively inhibit vital step/s is signalling pathways, in the normal function of the cancer cell, leading to apoptosis
- differentiating agents, which can include the active metabolite of Vitamin $D_3$ and novel analogues, retinoic acid and analogues.
- repair inhibiting drugs, which can inhibit the repair of damage induced by chemotherapeutic drugs or radiation
- prodrugs which when activated lead to a reduction in cellular thiol/sulphhydryl levels
- prodrugs which when activated will act directly or indirectly on oncogene or tumour suppressor gene or their gene products to influence tumour growth
- assayable substances or indicator molecules, including coloured or fluorescent substances such as fluorescein, raodiolabelled agents, substances which exist in differently coloured forms when free or chemically combined (e.g. dyes in colored and leuko-form), antigenic markers etc.

Prodrugs according to the invention mayl be employed either alone or in different combinations and sequences to identify the most effective drug regime.

The invention allows the selective delivery of the therapeutically active agent preferentially to those cells containing tyrosinase. The invention has the advantage of not relying on antibodies to target an enzyme to the tumour site, as used in the targeting strategy referred to as ADEPT (Antibody directed enzyme prodrug therapy).

The invention in a preferred embodiment provides a selective method for the treatment of malignant melanoma, an aggressive tumour which contains the enzyme tyrosinase. The invention may also be applicable for the treatment of other malignancies where tyrosinase is present in tumour cells, in particular breast carcinoma. The rapid expansion of the area of molecular biology and more specifically the use of retroviruses to transform cells into tyrosinase producing type, would allow a wide variety of future applications for our novel drug delivery system.

The invention can be applied for therapy to systems where selective expression of tyrosinase can successively be induced. Furthermore, the use of tyrosinase enzyme inhibitors, as small molecules or on polymer supports, can be used in conjunction with the delivery system of the invention to inactivate circulating tyrosinase, as found in melanoma patients, prior to prodrug administration. Such measures will be made to increase the degree of selectivity for melanoma cells in solid tumours.

It will be appreciated that the prodrugs provided according to the invention essentially consist of chemically modified drugs wherein the biological activity of the drug has been substantially eliminated. After administration the unmodified drug is released after the action of the enzyme tyrosinase. The release mechanism of the drug is dependent on the action of the enzyme tyrosinase, and generally occurs by a post enzyme oxidation, cyclization and hydrolysis to release the unmodified drug.

The action on tumour cells depends on the fact that certain cancer cells contain the enzyme tyrosinase, either naturally as in malignant melanoma or resulting from a spontaneous gene mutation as is reported during dedifferentiation of cancer cells or by transfection of cancer cells as in the use of retrovirus to express tyrosinase in non-pigment producing cancer cells.

The novel approach to cancer therapy according to the invention is thus based on a tyrosinase-activated drug delivery mechanism which relies on the spontaneous reductive cyclization of dopaquinone (and analogues) to render labile a potentially hydrolysable link between a nitrogen-containing group in the prodrug of formula TyrX—B—ThrAg*. This enables the specific release of the drug in melanogenic cells, as evidenced by data presented herein.

As indicated previously a wide range of therapeutically active substances can be chemically modified to form prodrugs in accordance with the invention. Preferably, these include antineoplastic agents which are already in use in the treatment of melanoma. "Combination chemotherapy for disseminated malignant melanoma". K L Abbott & G S Harman. Anti-cancer drugs 6:489–497). However, synthesis of novel prodrugs may lead to the utilization of available antineoplastic agents which are regarded as having no activity against this disease.

Examples include:

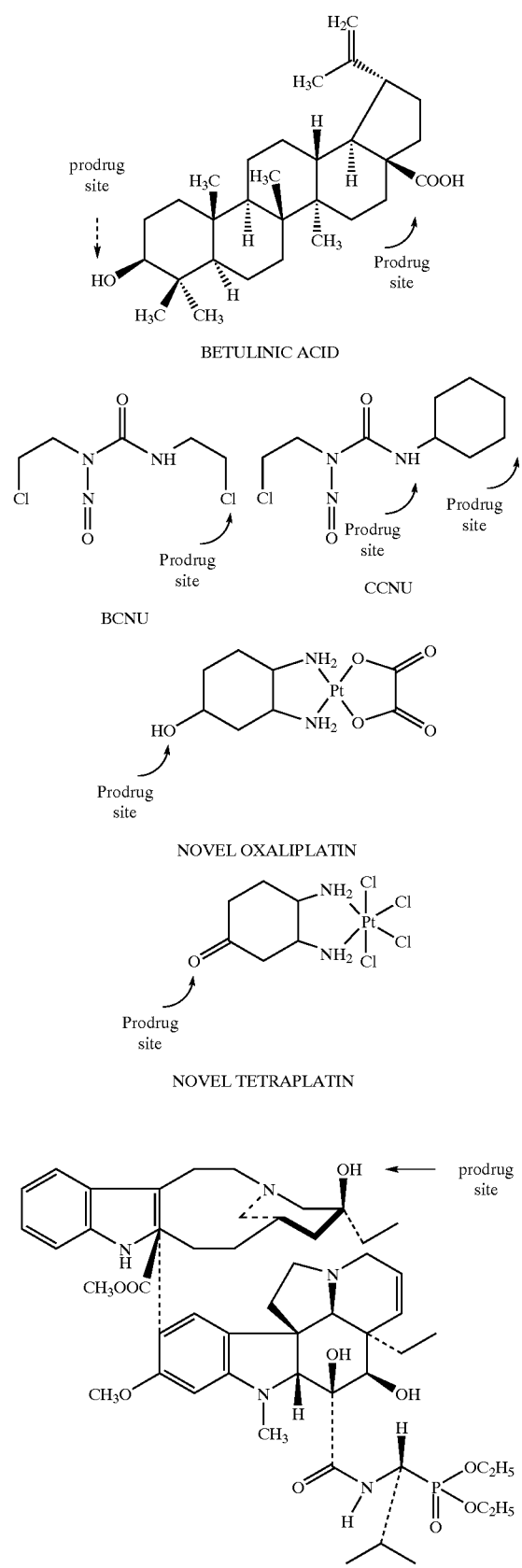

Vinca alkaloid, S12363. An example of an agent which is too active for clinic use. Modification/incorporation of this type of molecule may provide a potent active agent being released at the tumour site.

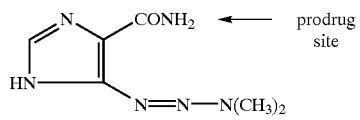

analoques of Dacarbazine 5-(3,3-Dimethyl-1-triazenyl)-1-H-imidazole-4-carboxamide (DTIC)

Furthermore, the therapeutically active agent can also refer to:

a chemosensitising agent, a chemical that can make tumour cells sensitive to cytotoxic agents, such as a resistance or multidrug resistance (MDR) modifier for example Nifedipine and S9788-2, the latter being a triazine derivative which contains chemical features known to be important for MDR reversing activity, planar aromatic domain and two amino groups, one having cationic charge at physiological pH. These agents can reverse the effect of multidrug resistance expression in refractory tumour cell lines, leading to a re-sensitisation of the tumour cells to MDR drugs:

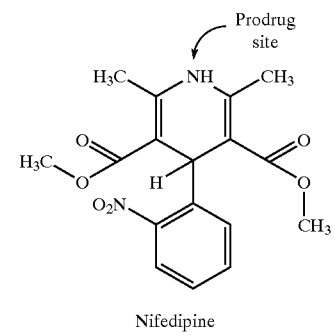

Nifedipine

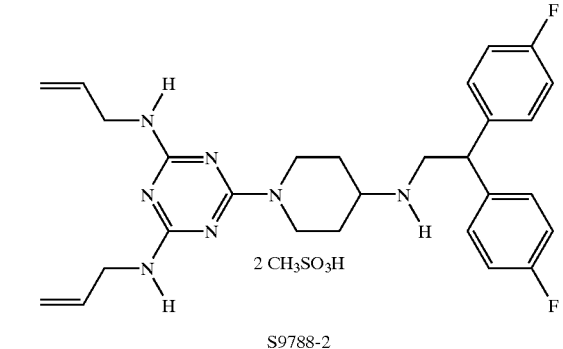

S9788-2 an apoptosis inducing agent, such as Staurosporin which inhibits calcium dependant phosphorylation leading to apoptosis of most types of cells.

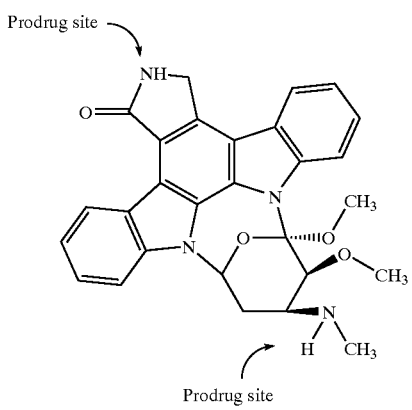

Prodrug site

Prodrug site

Staurosporin an apoptosis-inducing agent a signal transduction inhibitor, such as Quercetin or Genistein, a chemical that can inhibit the signalling pathway, such as phosphorylation of tyrosine and threonine which is essential for normal cell function.

TYROSINE KINASE INHIBITORS

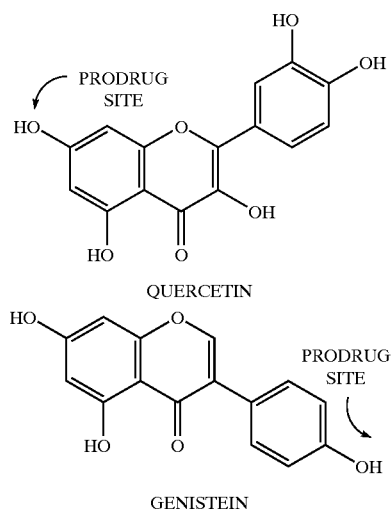

PRODRUG SITE

QUERCETIN

PRODRUG SITE

GENISTEIN an immunostimulating agent, a chemical that can prime the immune system, thus triggering the immune system against the tumour, either directly or indirectly. An example of this can be by reducing the levels of Nitric oxide, by inhibiting the enzyme Nitric oxide synthetase with N-methylarginine thus removing the immunosuppressive effect on high levels of Nitric oxide,

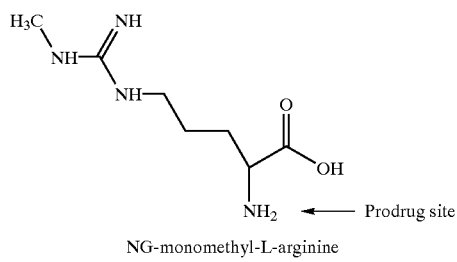

Prodrug site

NG-monomethyl-L-arginine incorporation of cytokines (TNF-α, IFN-α, IFN-γ or fragments of immunogenic chemicals) into a prodrug structure which can have immunomodulatory activity or other direct/indirect inhibitory actions on cancer cells, a differentiating agent, which can include the active metabolite of Vitamin $D_3$ and novel analogues such as Calcipotriol, retinoic acid and its analogues.

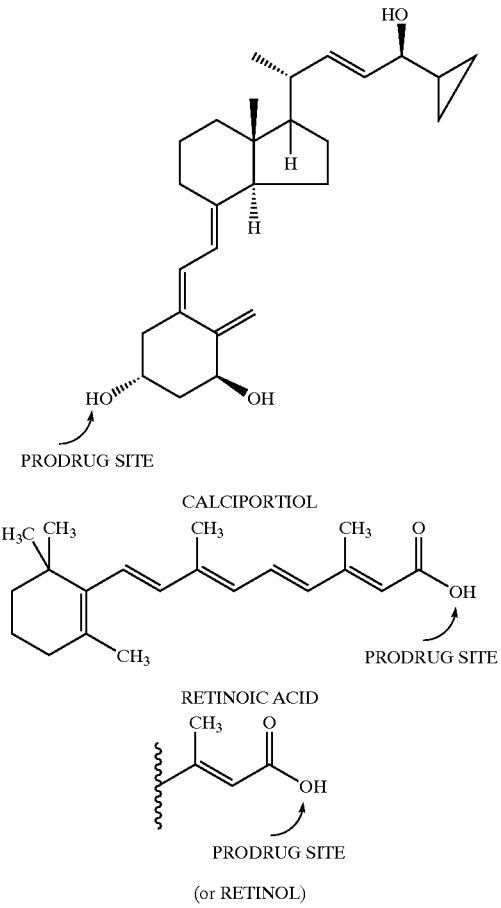

PRODRUG SITE

CALCIPORTIOL

PRODRUG SITE

RETINOIC ACID

PRODRUG SITE (or RETINOL)

a DNA repair enzyme inhibiting drug, such as O6-benzylguanine, which can inhibit the enzyme responsible for repairing nuclear DNA damage induced by chemotherapeutic drugs or radiation, a chemical, such as p-hydroxy anisole which when activated to the quinone leads to a reduction in cellular thiol/sulphhydryl levels rendering cells more susceptible to damage by chemical agents. Use of analogues of Buthionine sulfoximine (BSO) a glutamyl cysteine synthetase to reduce the level of cellular glutathinone synthesis (Kable et al [1989] Cancer Res, 49: 2327–2331)

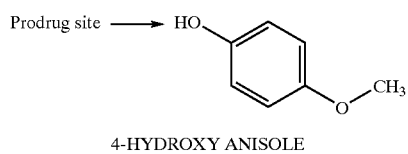

Prodrug site

4-HYDROXY ANISOLE an antisense molecule, which when activated will act directly or indirectly on oncogene or tumour suppressor gene or their gene products to influence tumour growth.

The prodrugs of the invention which can be synthesized by the initial formation of the activated mixed anhydrides of the selected agents which are then converted to the potential prodrug by nucleophilic attack by tyrosine. The general systemic cytotoxicity of the prodrugs will be diminished by incorporation of the reactive functional groups in the covalent bond to the tyrosine.

The invention further provides the use of the compounds of the invention in which are capable of conversion to an assayable substance in diagnostic and assay procedures. These include assay procedures for detecting the presence of tyrosinase enzyme in tissue samples and body fluids. In such assays, the sample to be assayed may be contacted with the compound of the invention and following an appropriate incubation period, the release of assayable substance detected. Such procedures are of particular use in the diagnosis of disease states where levels of tyrosinase enzyme are altered, as in melanomas associated with elevated tyurosinase levels.

DESCRIPTION OF FIGURES

The invention will now be described in more detail by reference to the appended Figures as well as in the following examples and descriptions of pilot studies, and chemical and biological tests. The Synthesis Examples illustrate the preparation of prodrugs in accordance with the invention.

In the Figures.

EXAMPLES

A. Pilot Study

Figure 1:
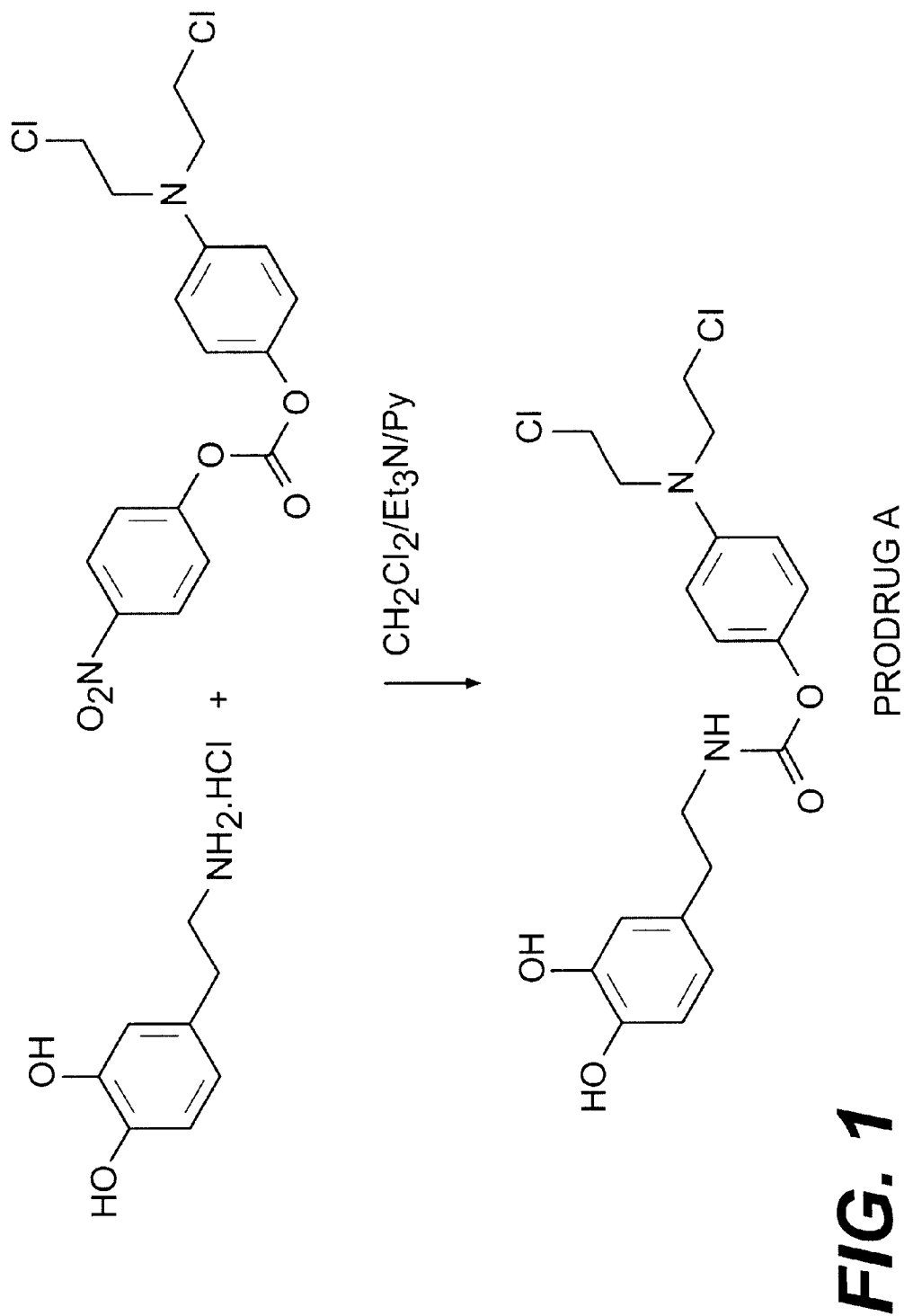
FIG. 1 illustrates a reaction scheme (Scheme 1) for producing Prodrug A
Figure 2:
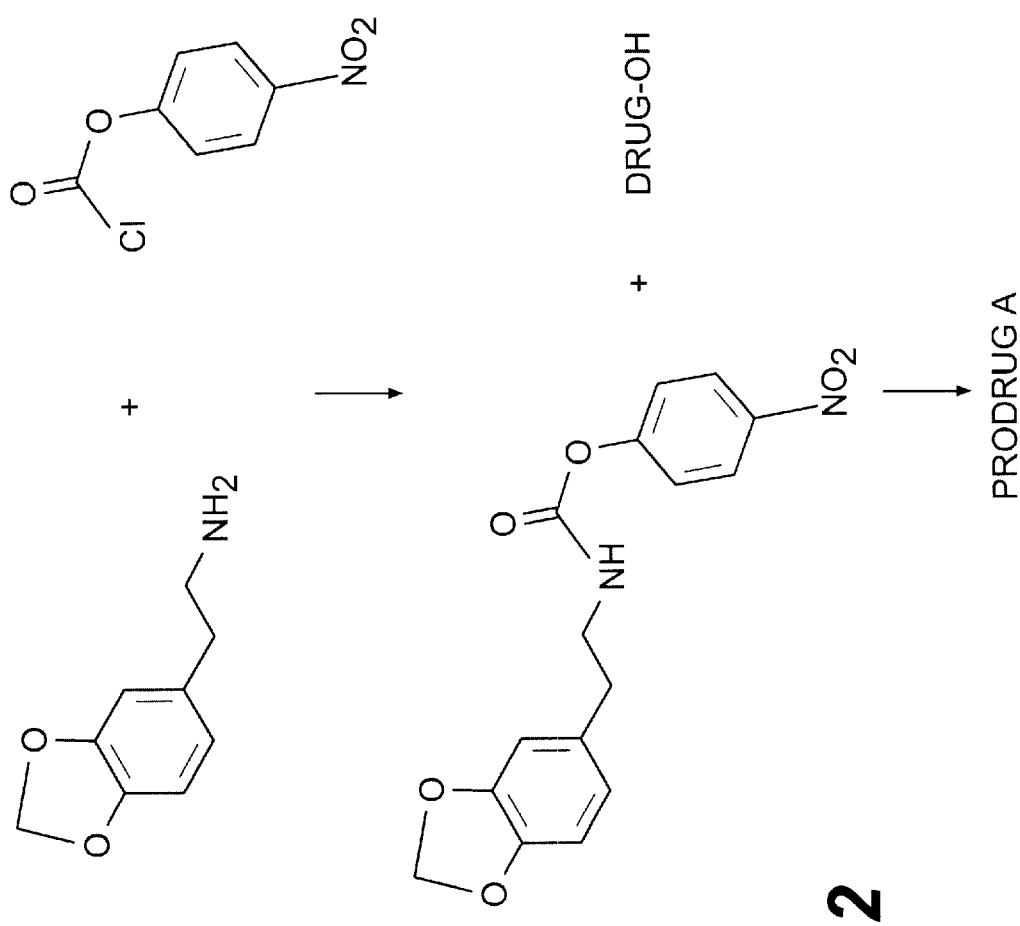
FIG. 2 illustrates a reaction scheme (Scheme 2) for producing Prodrug A
Figure 3:
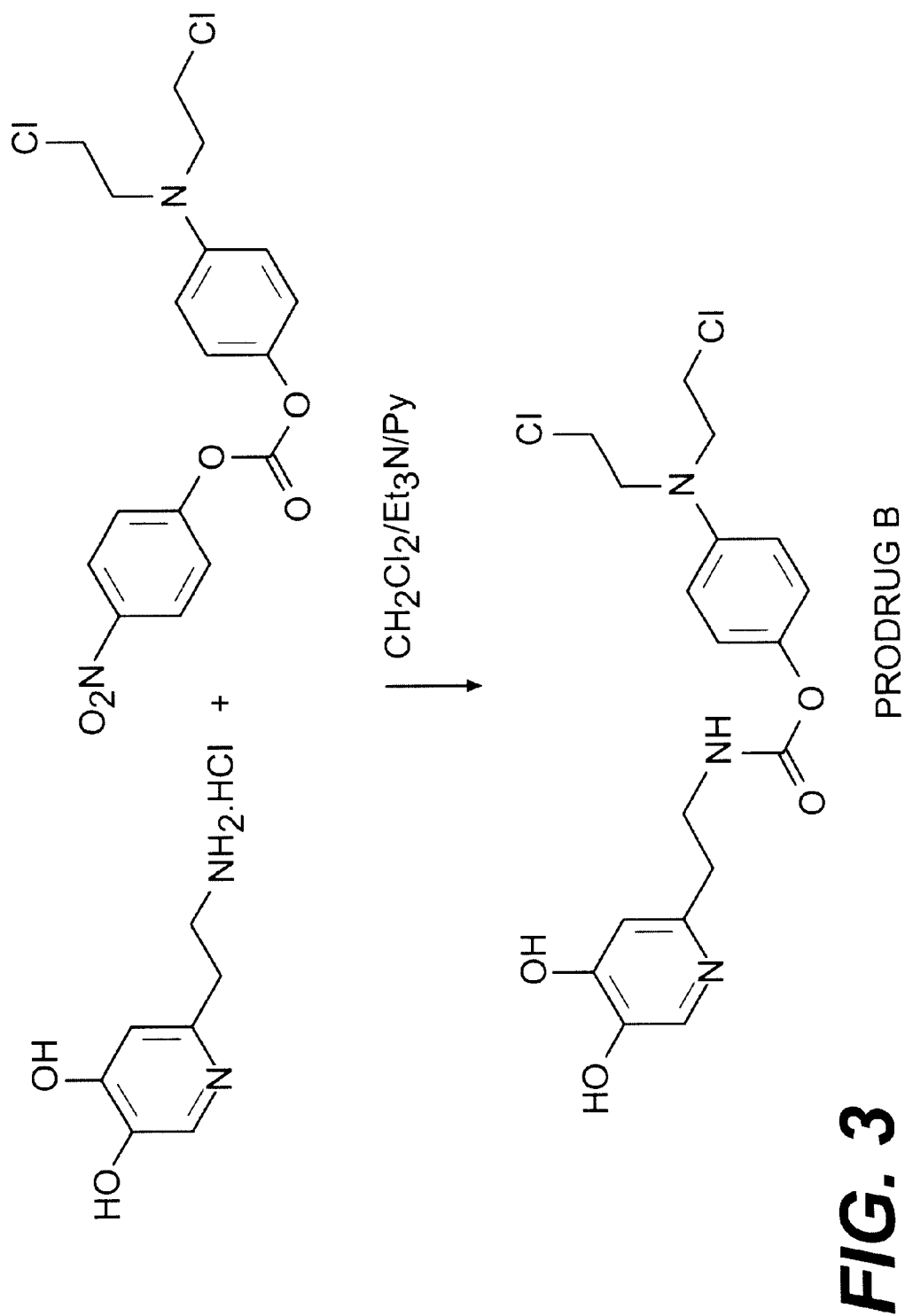
FIG. 3 illustrates a reaction scheme for producing Prodrug B
Figure 4:
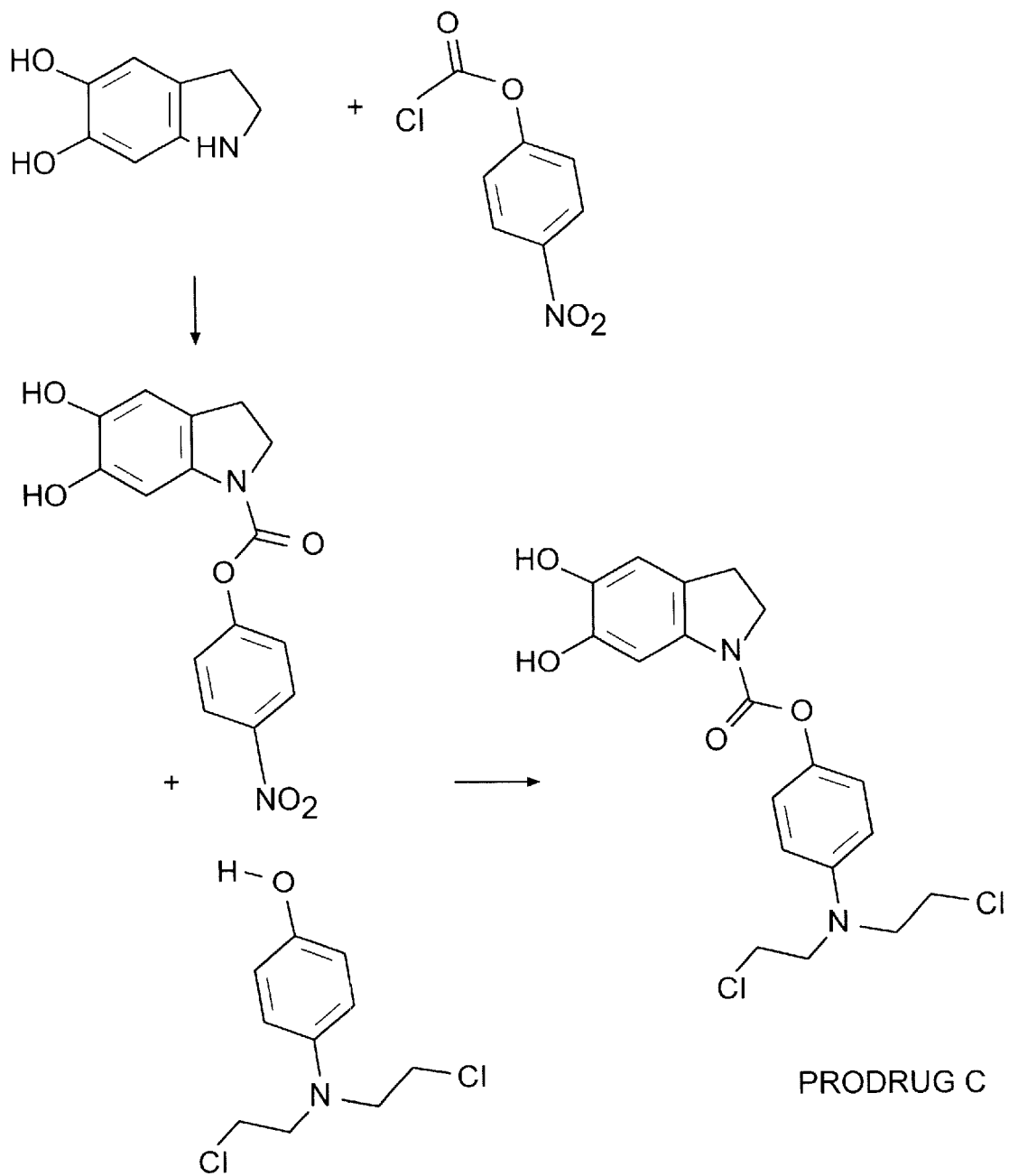
FIG. 4 illustrates a reaction scheme for producing Prodrug C
Figure 5:
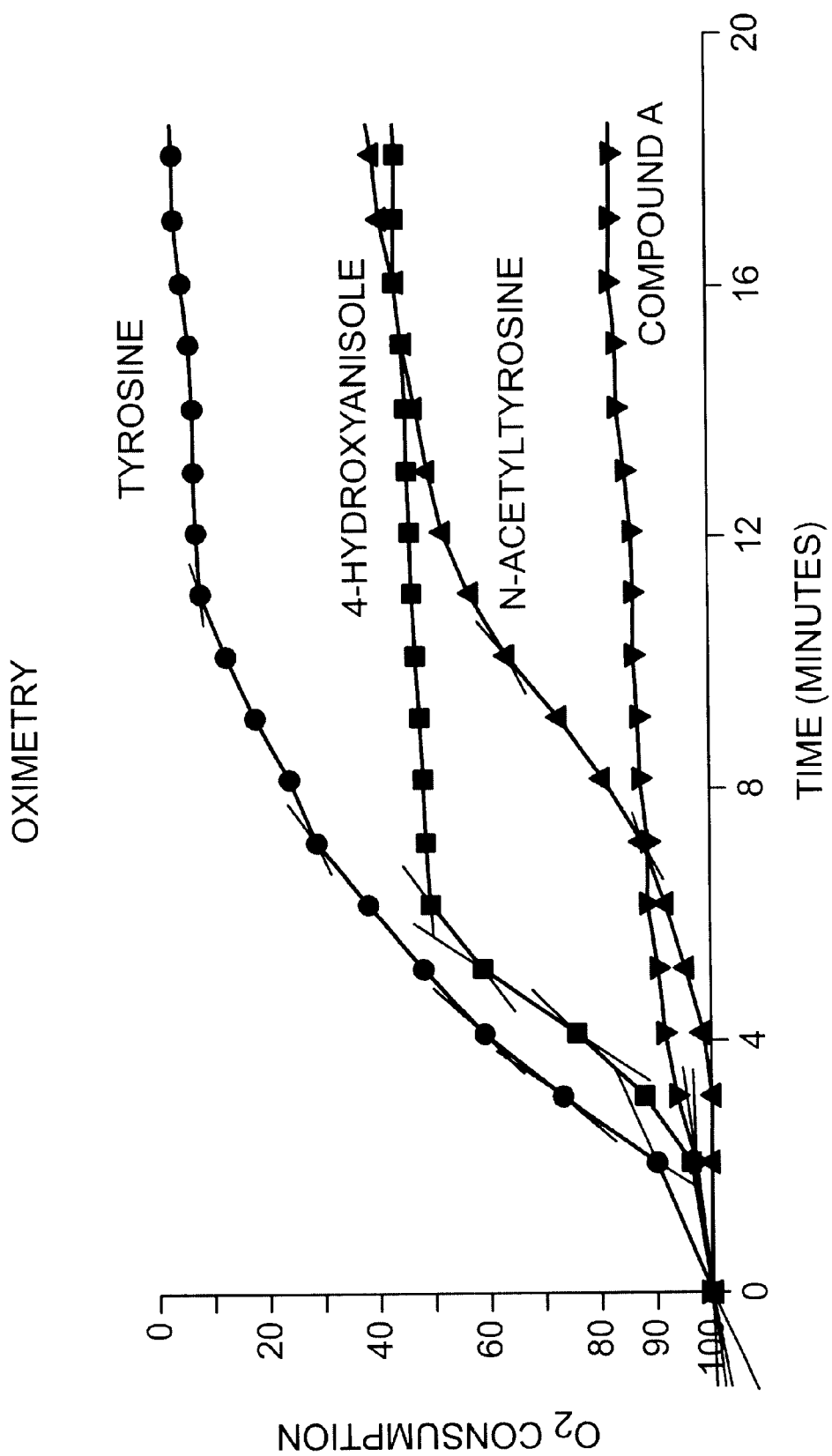
FIG. 5 illustrates the rsults of oximetry measurements on representative compounds

To test the feasibility of the tyrosinase-activated drug-release mechanism, a prodrug analogue was synthesized by covalent addition of 4-nitrophenyl isothiocyanate and dopamine. This yellow prodrug analogue was tested to establish whether, on oxidation and cyclization according to our proposed mechanism, it would yield the orange hydrolysis product 4-nitroaniline.

The prodrug analogue was stable in solution at pH 6.5 for up to 12 hours, but on addition of tyrosinase, an orange product was formed. Extraction with ethyl acetate isolated a compound different from the prodrug with strong absorption at 365 nm and properties consistent with 4-nitroaniline.

B. Synthesis Examples

1. Synthesis of N-(N-bis-chlorethyl-4-aminophenyloxycarbonyl)-3-hydroxy-tyramine (Prodrug A—Scheme 1)

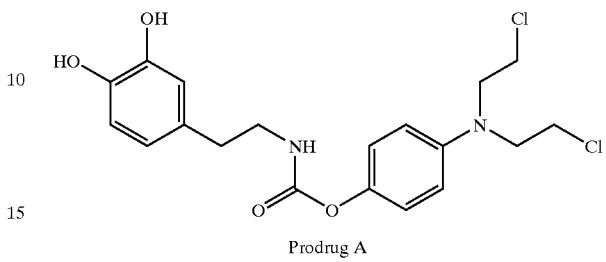

Prodrug A 1.0 g, 5.27 mmol of 3-hydroxytyramine hydrochloride was mixed with 20 ml of dry dichloromethane. To the stirred suspension 1 ml of triethylamine was added, followed by 1 ml of pyridine. The suspension was stirred for 5 min and then mixed with 2.32 g, 5.27 mmol of N-bis-chloroethyl-aminophenyloxy-p-nitro-phenyloxycarbonate. The suspension was stirred for 4 days at room temperature. The deep yellow solution was concentrated in vacuo. The residue was dissolved in ethyl acetate and washed with 0.1 M hydrochloric acid, 0.5 M sodium hydrogencarbonate solution, and distilled water. The organic fraction was dried over sodium sulphate, filtered and concentrated in vacuo. The residue was chromatographed on silica gel using gradient elution with ethylacetate and ethanol, resulting in 490 mg of a yellow solid. Rf=0.7(1:1 Ethylacetate: Ethanol), Mpt=80° C. (dec.), $^1$HNMR (D$^6$-DMSO):

2. Modified synthesis of p-N,N-Bis-chloroethyl-aminophenoxy-carbonyl-p-nitrophenoxide (Prodrug A—Scheme 2)

To a refluxing solution of p-nitrophenol chloroformate (4 g, 0.002 mol) in benzene (50 ml), a solution of N,N-bis-chloroethyl-aminophenoxide triethylammonium salt (5.4 g, 0.02 mol) in benzene (60 ml) was added dropwise over 15 min. The reaction mixture was refluxed under an inert atmosphere for 2 hs. The cooled reaction mixture was concentrated in-vacuo and chromatographed on silica using dichloromethane. The product was isolated from the early fractions (1–6) and then solidified with hexane. The required product was crystallised from benzene/hexane to result in a total of 7 g p-N,N-bis-chloroethyl-aminophenoxy-carbonyl-p-nitrophenoxide (80% yield, Rf=0.63 (CH$_2$Cl$_2$).

C. Silver Oxide Oxidation

Since the initial experiment provided evidence of the postulated reaction mechanism a prodrug containing an alkylating agent was synthesized (Compound A above). Chemical investigations showed that after silver oxide oxidation two compounds are liberated at pH 6.0 one polar with characteristics of the indole produced during the cyclization and hydrolysis reaction and one less polar with an Rf on thin layer chromatography similar to the mustard drug (Compound C).

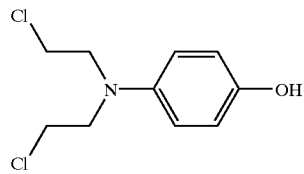

compound C

D. Biological Methods

1. Oximetry

To test the selectivity of the tyrosinase-activated delivery system, the ability of mushroom tyrosinase to catalyse the oxidation of various substrates was further examined by oximetry. The substrates tested were tyrosine (the normal enzyme substrate), Compound A, 4-hydroxyanisole and N-acetyl tyrosine.

The method of oximetry used has been described previously (Naish-Byfield & Riley 1992, Biochem J.288:763–67; Naish-Byfield et al 1994, Biochem J. 304: 155–162). Mushroom tyrosinase was obtained from Sigma, UK. Specific activity of the enzyme was 2200 units/mg of protein. The standard reaction mixture was made up of 2 ml of 100 $\mu$M of substrates (200 nmol/reaction) and 165 units of tyrosinase/ml added in volume of 200 $\mu$l. The reaction was performed in an oxygen-electrode chamber at room temperature. The utilization of oxygen with respect to time was monitored using a standard oxygen probe.

The results showed that Compound A is oxidised by tyrosinase, although the rate of the reaction was lower than for the normal substrate. 4-Hydroxyanisole and N-acetyl tyrosine were also oxidised, but at a lower rate than tyrosine.

2. Tyrosinase activity of test cell lines

The tyrosinase activity of five cell lines was measured when in logarithmic phase of growth. The tyrosinase activity was measured using the MBTH assay which has been described previously (Pifferi & Baldassari 1973, 52:325–335). Briefly tyrosinase activity is estimated by using Besthorn's hydrazone which indicates the generation of quinone formation.

Figure 6:
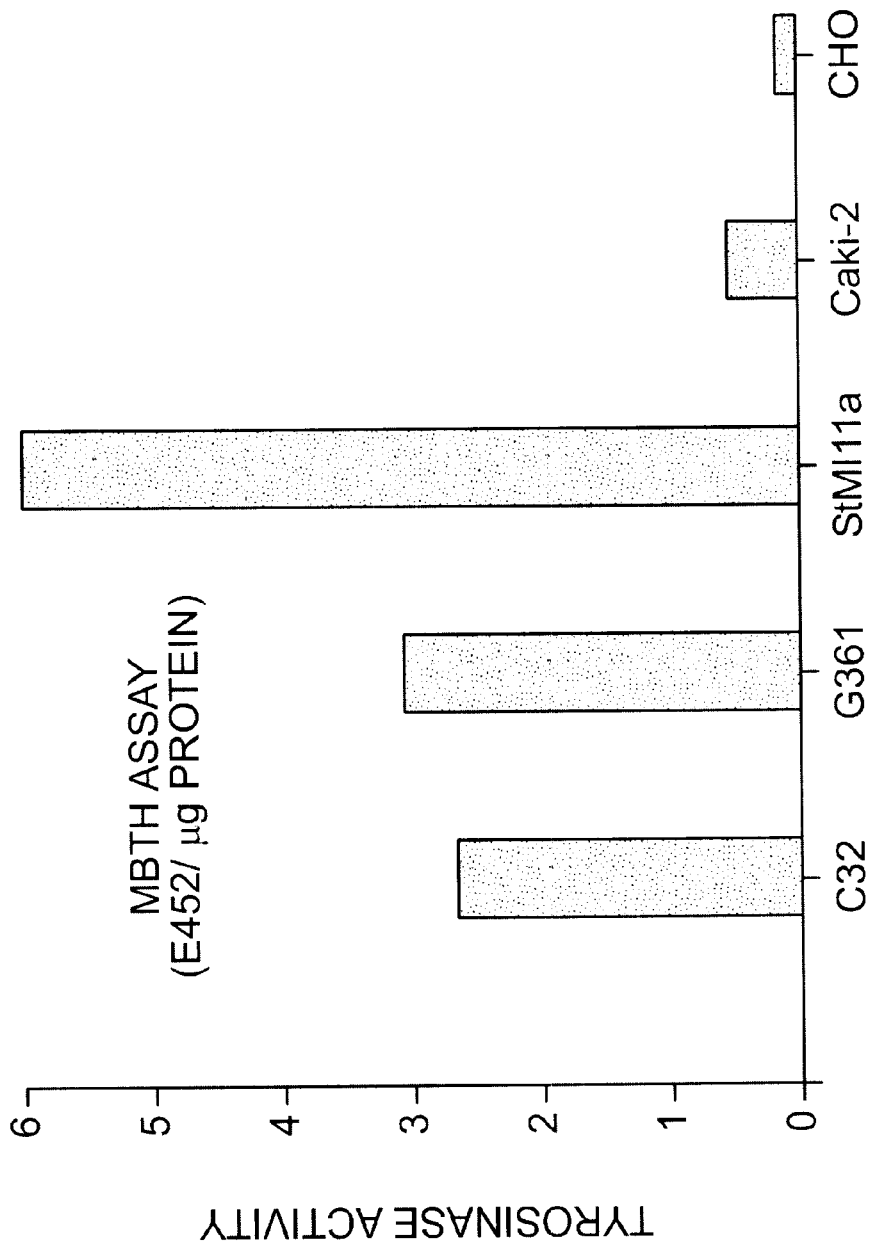
FIG. 6 illustrates the results of MTBH assays on five cell lines

The comparative tyrosinase activity of the five cell lines, as estimated by the MBTH assay is shown in FIG. 6 It can be seen that the three melanoma cell lines, C32, G361 and StMl11a is exhibited a high level of tyrosinase activity. The cell line Caki-1 (a renal cell carcinoma line) showed a small, but nonetheless measurable level of tyrosinase activity. The CHO cell line showed no detectable tyrosinase activity.

3. Measurement of growth inhibition (cytotoxicity)

The activities of the prodrug A, Compound B and the reference drug C, were compared for their ability to produce growth inhibition of human melanoma (C32, G361 and STMl11a) and nonmelanoma derived cell lines (Caki-2 and CHO) in vitro.

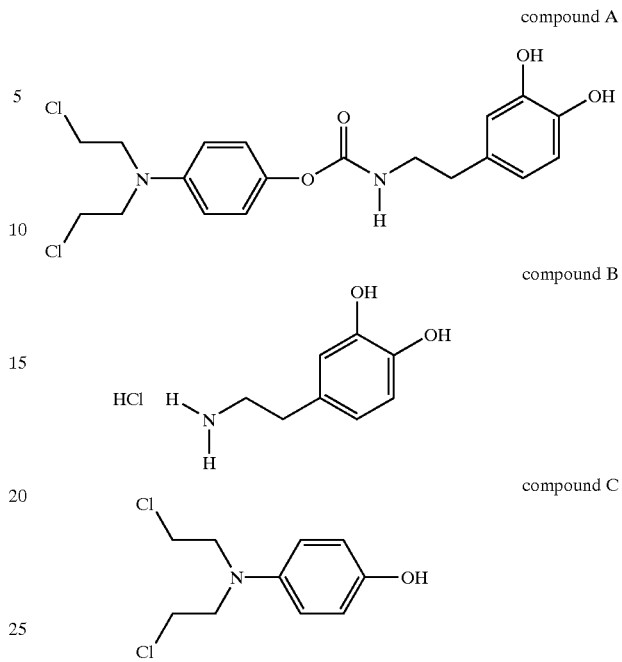

Growth inhibition was measured using the Sulpforhodamine B (SRB) assay as previously described (Skehan et al 1990; J.Natl Cancer Inst 82:1107–1112; Houghton et al 1994; Planta Medica, 60: 430–433). Cell lines C32 and Caki-2 were obtained from the ETCC (PHLS, Porton Down, UK). StM111a was kindly received from Dr. Zouboulis, Dept of Dermatology, Free University of Berlin, Germany. CHO cells were obtained from Dr. Smith, Richard Dimbleby Dept of Cancer Research, St Thomas Hospital, London. Cells were maintained in RPMI-1640 containing 10% heat-inactivated FCS, 2 mM L-glutamine, 50 IU/ml penicillin, 50 $\mu$g/ml streptomycin and 2.5 $\mu$g/ml amphotericin B, (Hyclone, UK). Cultures were incubated at 37° C. in 5% $CO_2$ in a humidified atmosphere. The SRB assay estimates cell number indirectly by measuring total basic amino acids.

Certain criteria were satisfied before using this technique. Firstly, it was established that optical density was directly proportional to cell number up to the density reached by the end of the assay. Secondly, an optimal starting density was found which allowed cells to remain in log-phase throughout the treatment and post-treatment period. Cultures were exposed to the test substances for 1 hr, a day after being plated. Assays were terminated 6 days after treatment, a period equivalent to 4–5 doubling times.

The activity of test substances A, B & C were compared by determination of the $IC_{50}$ value (concentration necessary to inhibit 50% of growth).

Figure 7:
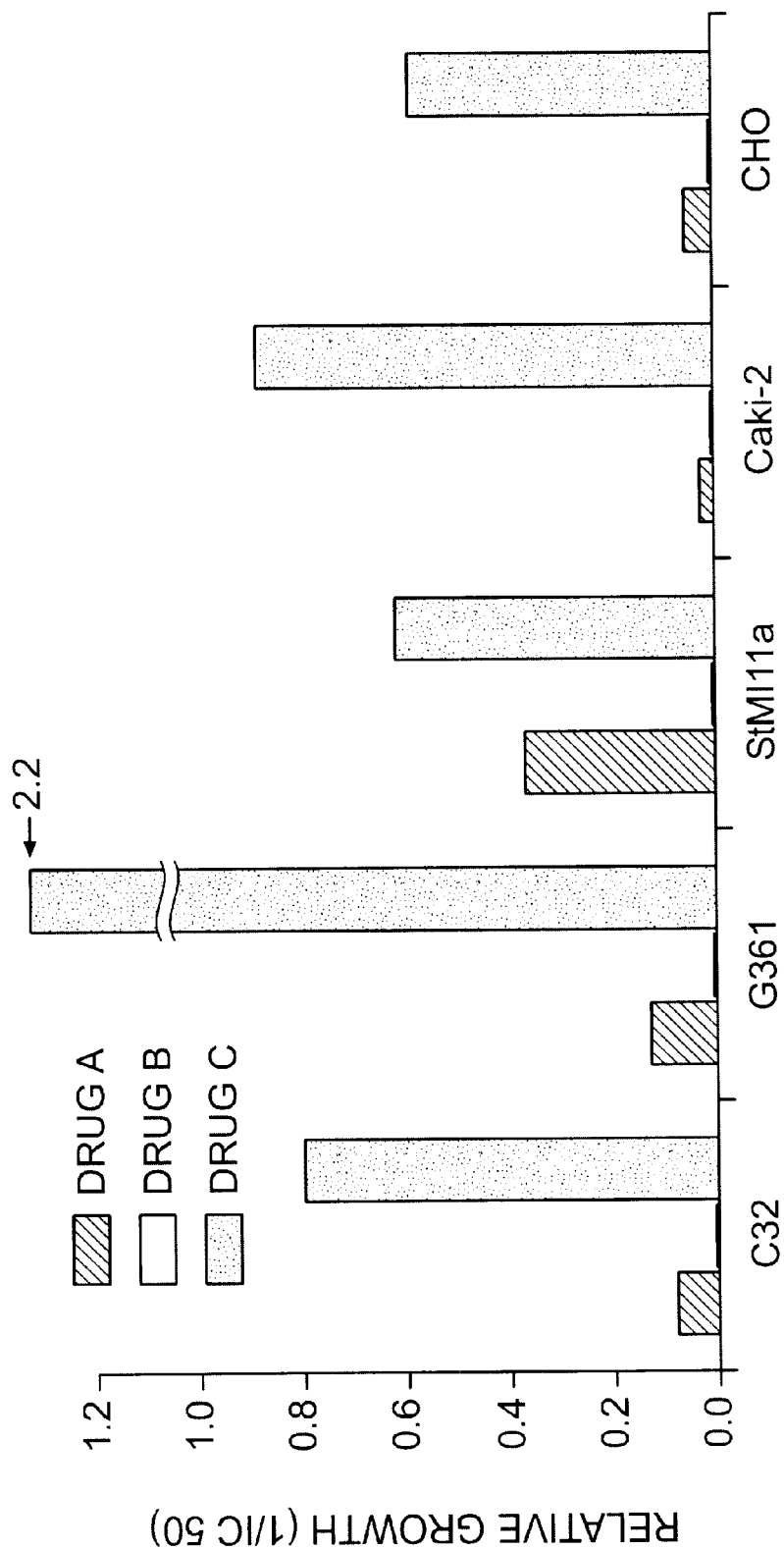
FIG. 7 illustrates the results of cytotoxicity tests
Figure 8:
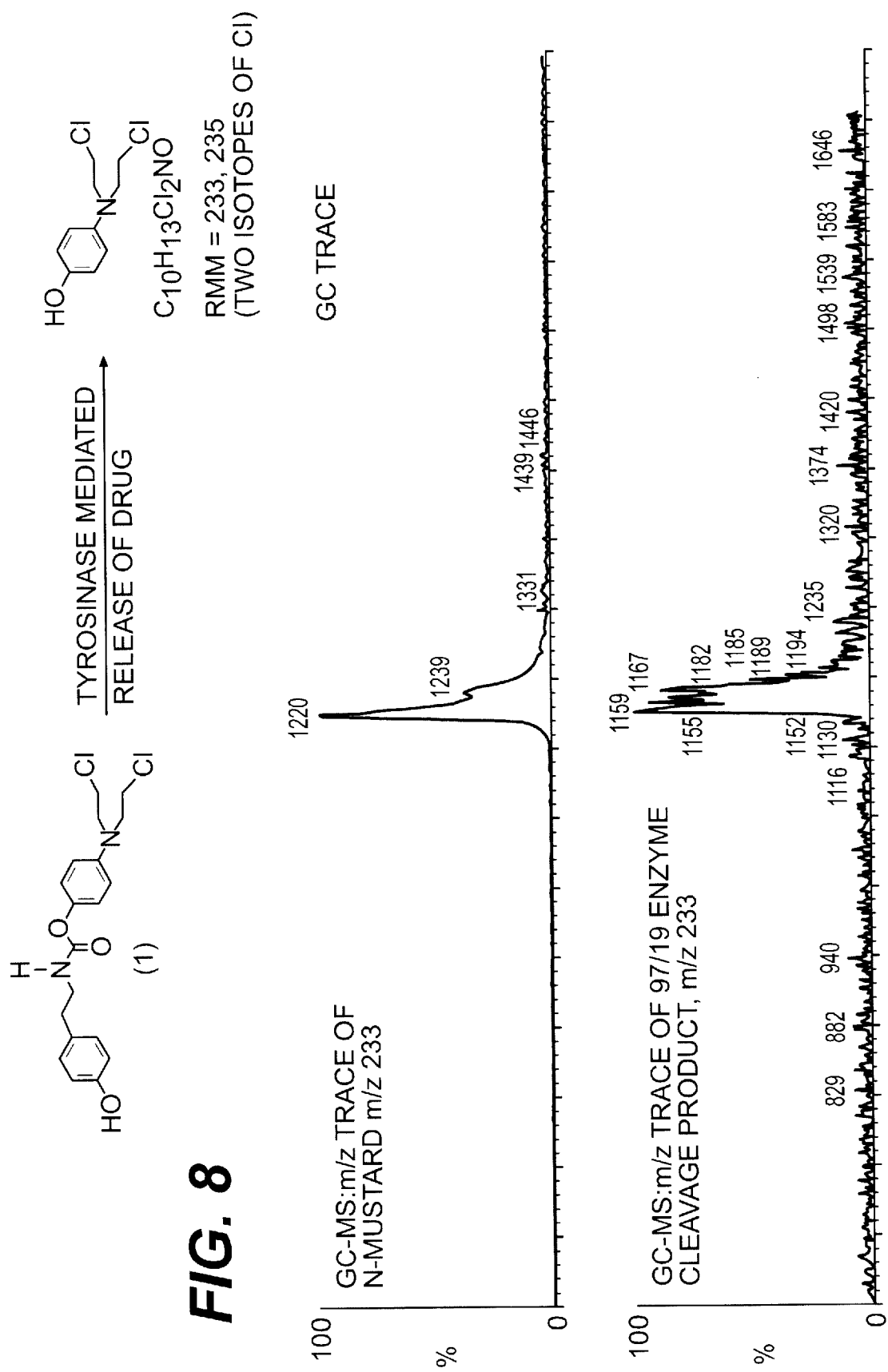
FIGS. 8 & 9 illustrates the results of experiments demonstrating the release of drug from prodrug
Figure 9:
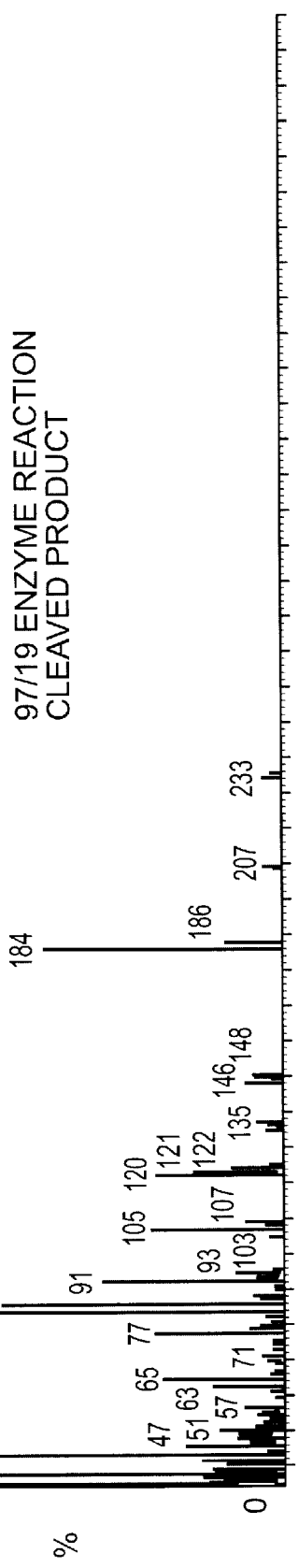
Figure 9:
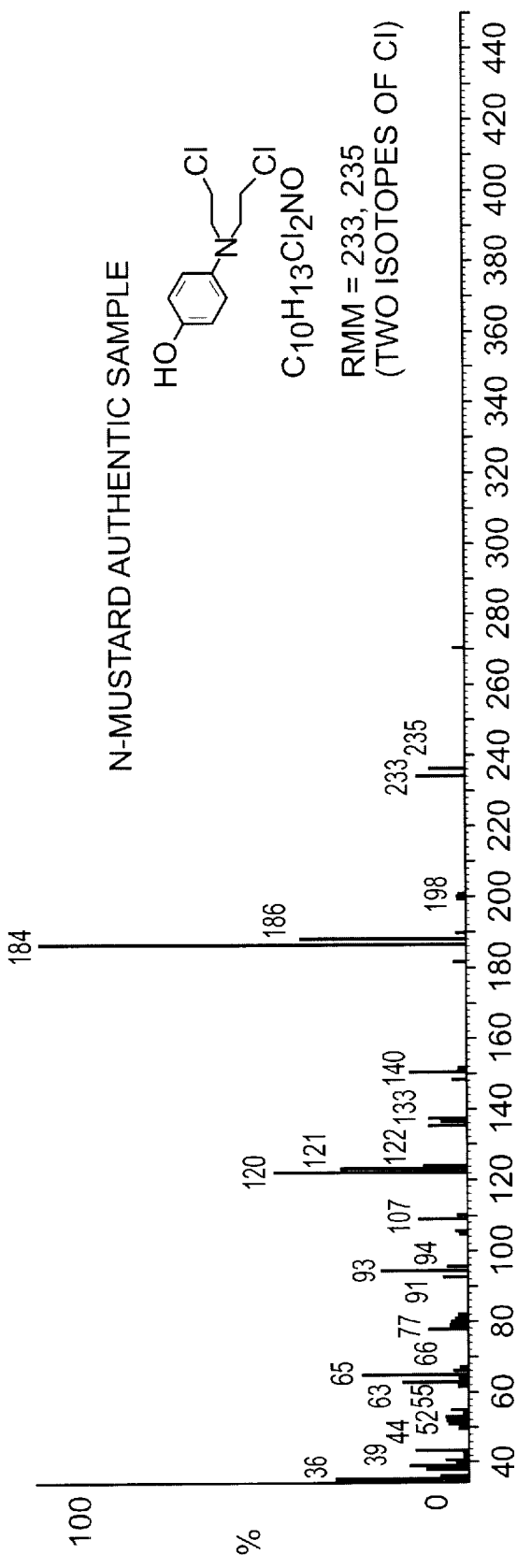

The relative toxicity of compounds A, B and C in each cell line (expressed as the inverse of the $IC_{50}$ determined by the sulphorhodamine assay after four hours exposure to the agents) is illustrated by the bar chart in FIG. 7. The data show that Compound B is essentially non-toxic compared to the reference Compound C, which exhibits an $IC_{50}$ between 1–2 $\mu$M in all cell lines.

By contrast Compound A (a prodrug according to the invention) is relatively non-toxic in non-melanogenic cells, but exhibits increasing toxicity with tyrosinase activity in the melanoma cell lines.

These data are entirely consistent with the postulated mechanism of the prodrugs of the invention and the cytotoxicity results are encouraging in demonstrating selective toxicity towards melanogenic cells.

E. Release of Drug from ProDrug (1) Upon Treatment with Tyrosinase

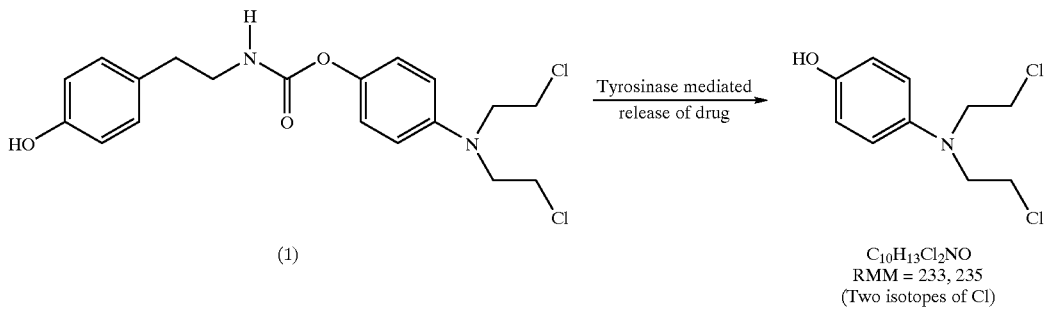

Prodrug (1) (2 mg, $5.1 \times 10^{-6}$ mol) was dissolved in DMSO (0.2 cm$^3$) and treated with a suspension of tyrosinase (2 mg, from Sigma) in phosphate buffer (0.2 cm$^3$, pH 7.2, from Aldrich). The resulting suspension was stirred at 25° C. for 1 hour. The reaction mixture was then analysed by thin layer chromatography, which demonstrated that a component of identical $R_f$ to the authentic mustard drug had been produced during this process. The solution was further analysed by GCMS (Fisons GC 8000 and Trio 1000 Mass Spectrometer using EI conditions) using an initial oven temperature of 150° C. for 5 minutes. The temperature was then raised from 150° C. to 250° C. over 5 minutes, and then maintained at 250° C. Under these conditions, both the authentic mustard drug and the drug which was released during the enzyme treated prodrug experiment had a retention time of 10.2 minutes. Furthermore, the mass spectra obtained from both the authentic and released mustard drug were identical and showed the expected isotope pattern for chlorine containing compounds, m/z (EI) 235 (M$^+$), 233 (M$^+$), 186 (M—CH$_2$Cl), 184 (M—CH$_2$Cl), 148 (M—CH$_2$—2Cl) and 120.

F. Summary

By way of summary, preliminary findings from the pilot study supports the feasibility of the novel drug delivery mechanism of the invention and these preliminary results were confirmed by the biological test procedures described herein.

It is envisaged that a range of agents with different modes of action can be incorporated in targeted prodrugs based on this release mechanism of the invention, including established cytotoxic agents with antimelanoma action such as mustards, nitrosoureas, vinca alkaloids and taxanes, novel plant products (betulinic acid which has some selectivity towards melanoma) as well as agents that modify the behaviour or sensitivity of tumour cells [see, e.g. Abbott K L & Harman G S (1995) Anti-Cancer Drugs, 6: 489–497]. These can include P170-multidrug resistance modifiers, inhibitors of DNA repair and modifiers of intracellular glutathione levels. We have found that melanoma can be sensitized to MDR-drugs in the absence of any staining for the MDR phenotype which is not normally detected by immunohistochemistry and western blotting. Our initial studies have concentrated on agents with known modes of action and relatively simple structures such as mustards and nitrosoureas which should present few synthetic obstacles. Those of skill in the art will readily be able to devise analogous synthetic schemes.

What is claimed is:

1. A method of treating melanoma in a patient comprising administering a compound that is capable of releasing a therapeutically active agent (ThrAg) at a desired location, said compound being a substrate for the tyrosinase enzyme and having the formula:

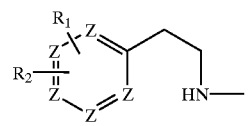

wherein TyrX— is a residue of an optionally substituted tyrosine analogue of the structure:

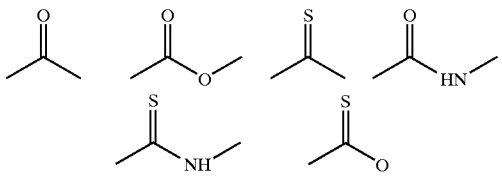

wherein each Z is independently selected from =CH—, —C—, =N—, and =N$^+$(O$^-$)—;

and $R_1$ and $R_2$ are independently selected from —H, —Br, —Cl, —I, —F, and —OH;

wherein B represents a linking group linking TyrX— and ThrAg* selected from:

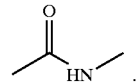

and wherein ThrAg* represents a residue of a therapeutically active agent ThrAg.

2. The method of claim 1 wherein $R_1$ and $R_2$ are independently selected from —H and —OH.

3. The method of claim 2 wherein $R_1$ and $R_2$ are hydrogen.

4. The method of claim 1 wherein B is

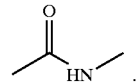

.

5. The method of claim 1 wherein the therapeutically active agent has the formula NH$_2$—ThrAg*.

6. The method of claim 1 wherein the therapeutically active agent has the formula HO—ThrAg*.

7. The method of claim 1 wherein the compound has one of the following formulae:

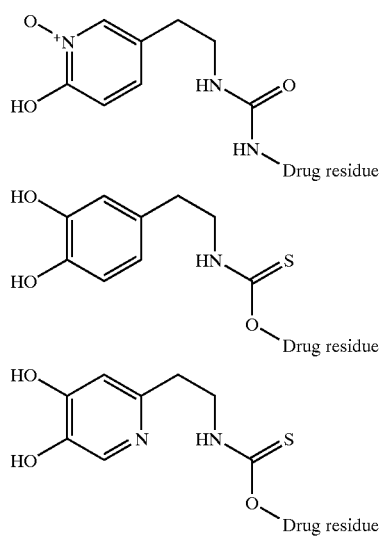
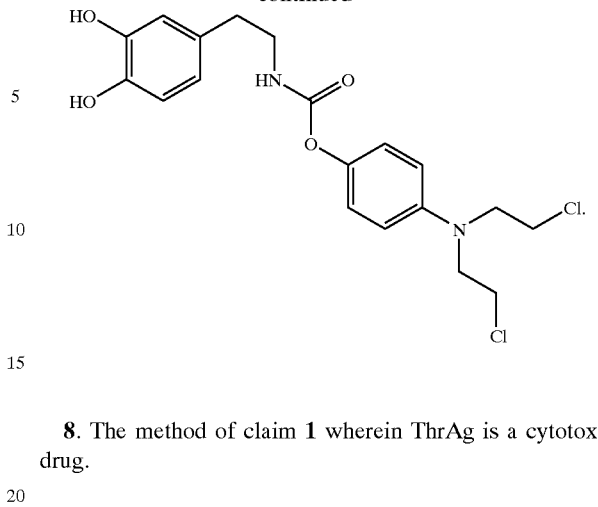
8. The method of claim 1 wherein ThrAg is a cytotoxic drug.
* * * * *

UNITED STATES PATENT AND TRADEMARK OFFICE
CERTIFICATE OF CORRECTION

PATENT NO. : 6,573,284 B1
DATED : June 3, 2003
INVENTOR(S) : Patrick Anthony Riley et al.

It is certified that error appears in the above-identified patent and that said Letters Patent is hereby corrected as shown below:

Title page,
After the Inventors, insert -- Assignee: Phairson Medical Ltd, Chelsea Harbour, London (GB) --.
After the *Primary Examiner*, insert -- *Attorney, Agent, or Firm*—Finnegan, Henderson, Farabow, Garrett & Dunner, L.L.P. --.

Column 16,
Line 34, "–C–," should read -- =C–, --.

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,573,284 B1
DATED : June 3, 2003
INVENTOR(S) : Patrick Anthony Riley et al.

It is certified that error appears in the above-identified patent and that said Letters Patent is hereby corrected as shown below:

<u>Title page,</u>
After the Inventors, delete "Assignee: Phairson Medical Ltd, Chelsea Harbour, London (GB)".

This certificate supersedes the Certificate of Correction issued September 23, 2003.

Signed and Sealed this

Twenty-fourth Day of February, 2004

JON W. DUDAS
*Acting Director of the United States Patent and Trademark Office*